(12) United States Patent
Corzani et al.

(10) Patent No.: US 6,498,201 B1
(45) Date of Patent: *Dec. 24, 2002

(54) LOW VISCOSITY THERMOPLASTIC COMPOSITIONS FOR STRUCTURES WITH ENHANCED MOISTURE VAPOR PERMEABILITY AND THE UTILISATION THEREOF IN ABSORBENT ARTICLES

(75) Inventors: Italo Corzani, Chieti (IT); Gianfranco Palumbo, Bad Homburg (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/701,936

(22) PCT Filed: Jun. 1, 1999

(86) PCT No.: PCT/IB99/00990

§ 371 (c)(1),
(2), (4) Date: Dec. 6, 2000

(87) PCT Pub. No.: WO99/64505

PCT Pub. Date: Dec. 16, 1999

(30) Foreign Application Priority Data

Jun. 9, 1998 (EP) ............................................ 98110596

(51) Int. Cl.⁷ ............................................... C08L 15/00
(52) U.S. Cl. ...................................... 523/111; 523/105
(58) Field of Search ................................ 524/315, 312, 524/385, 386, 387, 389; 523/105, 111

(56) References Cited

U.S. PATENT DOCUMENTS

| 4,713,069 | A | * | 12/1987 | Wang et al. | ................. | 604/378 |
|---|---|---|---|---|---|---|
| 4,854,995 | A | * | 8/1989 | Kasper et al. | ............... | 156/243 |
| 5,525,706 | A | | 6/1996 | Gruber et al. | ............... | 528/354 |
| 5,600,089 | A | | 2/1997 | Reed et al. | | |
| 5,753,782 | A | * | 5/1998 | Hammond et al. | ......... | 525/450 |
| 6,133,400 | A | * | 10/2000 | Helmke | ........................ | 528/83 |

FOREIGN PATENT DOCUMENTS

| DE | 33 05 473 | 2/1998 | |
|---|---|---|---|
| DE | EP 0 844 006 | 5/1998 | |
| EP | 0 134 455 | 3/1985 | |
| EP | 0 510 998 | 10/1992 | .............. C08J/5/18 |
| GB | WO 94/28061 | 12/1994 | ............ C08K/5/00 |
| WO | WO 94/16020 | 7/1994 | |
| WO | WO 95/02647 | 1/1995 | .......... C09J/129/00 |
| WO | WO 96/25902 | 8/1996 | |
| WO | WO 98/06375 | 2/1998 | |

\* cited by examiner

*Primary Examiner*—Edward J. Cain
*Assistant Examiner*—Katarzyna W. Lee
(74) *Attorney, Agent, or Firm*—Bart S. Hersko

(57) ABSTRACT

The present invention relates to thermoplastic compositions for making a liquid impermeable moisture vapor permeable layer by coating the composition onto a substrate. The thermoplastic compositions comprise preferred thermoplastic polymers and suitable hydrophilic plasticizers that also enhance the moisture vapor permeability of films or layers made from the thermoplastic compositions. The layers made from the thermoplastic compositions of the present invention can find a variety of applications wherein moisture vapor permeability is desirable, such as within absorbent articles for example diapers, sanitary napkins, panty liners and incontinence products, and also protective bedding covers, protective clothing and the like.

12 Claims, No Drawings

LOW VISCOSITY THERMOPLASTIC COMPOSITIONS FOR STRUCTURES WITH ENHANCED MOISTURE VAPOR PERMEABILITY AND THE UTILISATION THEREOF IN ABSORBENT ARTICLES

FIELD OF THE INVENTION

The present invention relates to thermoplastic compositions for making a moisture vapour permeable, liquid impermeable layer by coating the composition onto a substrate. The compositions of the present invention can find a variety of applications, wherein moisture vapour permeability is desirable for example within absorbent articles such as diapers, sanitary napkins, panty liners and incontinence products, protective bedding covers, protective clothing and the like.

BACKGROUND OF THE INVENTION

Thermoplastic films which provide a liquid barrier in addition to providing moisture vapour permeability are known in the art. Particularly preferred are hydrophilic continuous films that do not allow the flow of moisture vapour through open pores or apertures in the material, but do transfer substantial amounts of moisture vapour through the film by absorbing water on one side of the film where the moisture vapour concentration is higher, and desorbing or evaporating it on the opposite side of the film where the moisture vapour concentration is lower.

For example WO 95/16746 discloses films prepared from mixtures of a) block copolyether ester, block copolyether amides (e.g. Pebax™) and or polyurethane and b) thermoplastic polymer which is incompatible with a, and c) a compatibiliser. The films are liquid impermeable and have moisture vapour permeability of about 700 g/m$^2$·day. Also, U.S. Pat. No. 5,447,783 discloses a vapour permeable water resistant multi component film structure having at least three layers. The outer layers are hydrophobic copolyetherester elastomers having a thickness of 1.3–7.6 micrometers and a WVTR of 400–2500 g/m$^2$·24 h and the inner layer is a hydrophilic copolyetherester elastomer having a thickness of 7.6–152 micrometers and a WVTR of at least 3500 g/m$^2$·24 h.

U.S. Pat. No. 5,445,875 discloses a waterproof, bloodproof and virusproof breathable laminate. The laminate comprises a woven/nonwoven fabric and an extruded film such as Hytrel™ having a thickness of about 1 mil (25.4. micrometers).

Other composite laminates are described for example in U.S. Pat. No. 5,599,610 which discloses tri-laminated fabric for surgical gowns comprising outer layers of woven fabric and an inner layer of a microporous polyurethane membrane. The microporous film has a thickness of 12–55 micrometers and a MVTR of 1100 g/m$^2$·24 h upright and 5500 g/m$^2$·24 h inverted (ASTM E96-B). Polyetherpolyurethane adhesive is used to join the layers.

Similarly, U.S. Pat. No. 5,532,053 discloses a high moisture transmission medical film which can be laminated onto a nonwoven material. The laminate film comprises a first layer of polyetherester copolymer and second and third layers selected from a specified group of polymers. The film has a MVTR of greater than 750 g/m$^2$·24 h (ASTM F1249) and a thickness of less than 1 mil (25.4 micrometer) preferably 0.6 mil to 0.75 mil (15–19 micrometers).

U.S. Pat. No. 4,938,752 discloses absorbent articles comprising films of copolyether esters which have reduced water permeability, a water vapour permeability of 500 g/m$^2$·24 h (as measured in a specified described test) and a thickness of 5–35 micrometers. There is no disclosure of a supportive substrate.

U.S. Pat. No. 4,493,870 discloses a flexible layered waterproof product comprising a textile material covered with a film of a copolyetherester having an MVTR of at least 1000 g/m$^2$·24 h (ASTM E96-66) having a thickness of 5 to 35 micrometers.

GB 2024100 discloses a flexible layered water resistant article comprising a microporous hydrophobic outer layer which is moisture vapour permeable but resist liquids and a hydrophilic inner layer of polyetherpolyurethane having a MVRR of above 1000 g/m$^2$·24 h.

In our patent application Ser. No. 09/702,000 entitled "Low viscosity thermoplastic compositions for moisture vapour permeable structures and the utilisation thereof in absorbent articles" filed on the same day as the present application, thermoplastic compositions are disclosed for making hydrophilic continuous moisture vapour permeable, liquid impermeable layers having preferred characteristics of moisture vapour permeability and liquid imperviousness. The thermoplastic compositions comprise preferred thermoplastic polymers such as polyurethanes, poly-ether-amides block copolymers, polyethylene-acrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids and derivatives, ionomers, polyethylene-vinyl acetate with a vinyl acetate content of more than 28 weight %, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, or mixtures thereof. The disclosed preferred thermoplastic compositions are also readily processable so as to provide a coating having the desired thickness onto a substrate, so avoiding the need of complex traditional extrusion apparatuses. This is achieved by modifying the viscosity of the thermoplastic polymers by means of the inclusion in the composition of a suitable plasticiser that lowers such viscosity. This allows to utilise with these preferred compositions typical process conditions known in the art for the direct coating of low viscosities hot melts onto a substrate in order to form a moisture vapour permeable, liquid impervious film or layer.

It has surprisingly been discovered that by suitably selecting the plasticiser or blend of plasticisers a thermoplastic composition can be obtained for making a moisture vapour permeable, liquid impermeable film or layer, which has an enhanced moisture vapour permeability if compared to a corresponding film or layer made form a composition not comprising the plasticiser or blend of plasticisers. Of course the preferred plasticiser or blend of plasticisers can also adjust the viscosity of the thermoplastic composition to allow the production of a film or a layer from the thermoplastic composition by means of a simplified coating process.

SUMMARY OF THE INVENTION

The present invention relates to a thermoplastic composition for making a moisture vapour permeable, liquid impervious layer by coating said composition onto a substrate. The composition comprises:
a thermoplastic polymer or mixture of polymers selected from the group consisting of polyurethanes, poly-etheramides block copolymers, polyethylene-acrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids and derivatives, ionomers, polyethylene-vinyl acetate with a vinyl acetate content of more than 28 weight %, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, or mixtures thereof, a suitable compatible hydrophilic plasticiser or blend of hydrophilic plasticisers, wherein said thermoplastic composition has a viscosity of from 50 poise to 4000 poise at a frequency of 1 rad/s at a temperature of 210° C. or less and a viscosity of less than 2000 poise at a frequency of 1000 rad/s at a temperature of 210° C. or less, wherein said hydrophilic plasticisers are selected from the group consisting of acids, esters, amides, alcohols, polyalcohols, or mixtures thereof.

DETAILED DESCRIPTION OF THE INVENTION

Suitable thermoplastic polymers comprised in the composition according to the present invention include polyurethanes, poly-ether-amides block copolymers, polyethylene-acrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids and derivatives, ionomers, polyethylene-vinyl acetate with a vinyl acetate content of more than 28 weight %, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, and mixtures thereof.

Particularly preferred thermoplastic polymers are thermoplastic poly-ether-amide block copolymers (e.g. Pebax™), thermoplastic poly-ether-ester-amide block copolymers, thermoplastic polyester block copolymers (e.g. Hytrel™), thermoplastic polyurethanes (e.g. Estane™), or mixtures thereof.

Such thermoplastic polymers or mixture of polymers can be typically highly viscous in the melted state at the process conditions that are typical of the known processes of film or layer formation, e.g. an extrusion process involving a high power screw extruder. For example they may have a viscosity higher than 5000 poise at a temperature of 20° C. above the DSC (Differential Scanning Calorimetry) melting point, which is the temperature identified as that corresponding to the DSC peak, or corresponding to the highest DSC peak in case of a mixture of polymers showing more than one peak, and at a frequency of 1 rad/sec.

The viscosity of the preferred thermoplastic polymers or mixture of polymers can be preferably adjusted by including in the thermoplastic composition a suitable plasticiser, or blend of plasticisers, that is compatible with the thermoplastic polymers and that lowers the viscosity of the thermoplastic polymer or mixture of polymers in the melted state.

The thermoplastic compositions of the present invention comprising the preferred hydrophilic plasticiser or blend of hydrophilic plasticisers have the following complex viscosities ($\eta^*$):

50 poise<$\eta^*$<4000 poise, preferably 100 poise<$\eta^*$<2000 poise, more preferably 100 poise<$\eta^*$<1000 poise, at a frequency of 1 rad/s at a temperature of 210° C. or less and $\eta^*$<2000 pose, preferably $\eta^*$<1000 poise, more preferably $\eta^*$<500 poise, at a frequency of 1000 rad/s at a process temperature (T) of 210° C. or less, wherein $\eta^*$ represents the complex viscosity of the thermoplastic polymeric composition. Preferably the temperature T is 200° C. or less and more preferably 180° C. or less and most preferably from 200° C. to 50° C.

The thermoplastic compositions having the complex viscosity described allow for a film or layer to be coated onto a substrate using typical coating conditions and apparatuses known in the art for the coating of low viscosities hot melt compositions in a layer having a required thickness onto a substrate, while also keeping the advantageous characteristics of the preferred thermoplastic polymers in providing hydrophilic continuous moisture vapour permeable, liquid impermeable layers or films.

Thermoplastic compositions having such viscosities can also provide very thin films or layers.

It has been surprisingly found that by selecting the hydrophilic plasticiser or blend of hydrophilic plasticisers to be comprised in the thermoplastic composition from the group consisting of acids, esters, amides, alcohols, polyalcohols, or mixtures thereof, the advantage of an enhanced moisture vapour permeability of the resulting layer or film formed from the thermoplastic composition is achieved, when compared to a corresponding film or layer formed from a thermoplastic composition comprising the same thermoplastic polymer, but without the plasticiser.

The preferred hydrophilic plasticiser or blend of hydrophilic plasticisers can also adjust the viscosity of the thermoplastic composition to the preferred values in order to make it processable by coating said thermoplastic composition onto a substrate in a layer or film having a desired thickness.

Preferred hydrophilic plasticisers according to the present invention are citric acid esters, tartaric acid esters, glycerol and its esters, sorbitol, glycolates, and mixtures thereof.

Preferably the thermoplastic composition of the present invention comprises from 10% to 80%, more preferably from 25% to 70% by weight of the thermoplastic composition, of the thermoplastic polymer or mixture of polymers, and from 20% to 90%, preferably from 30% to 75% by weight of the thermoplastic composition, of the suitable hydrophilic plasticiser or blend of hydrophilic plasticisers.

The thermoplastic compositions of the present invention may in addition comprise additional optional components to further improve the processibility of the compositions and also the mechanical characteristics as well as other characteristics as tackiness, resistance to ageing by light and oxygen, visual appearance etc., of the films or layers formed from such thermoplastic compositions.

Such optional components include tackifying resins or blends of tackifying resins having a softening point of 125° C. or less. Preferred resins, which may be present by up to 50% by weight of the thermoplastic composition, may be selected from rosins and rosin esters, hydrocarbon resins, aliphatic resins, terpene and terpene-phenolic resins, aromatic resins, synthetic $C_5$ resins, mixtures of synthetic $C_5$–$C_9$ resins, and mixtures thereof. Other optional components of said thermoplastic compositions include anti-oxidants, anti-ultraviolets, pigments and mixtures thereof, which may be present within the composition at a level of up to 10% by weight of the composition.

A thermoplastic composition according to the present invention can be manufactured with a process that will typically comprise the steps of providing the thermoplastic polymer or mixture of polymers and the suitable plasticiser or blend of plasticisers, heating the components and compounding them, e.g. with a known suitable mixer to form the thermoplastic composition in the molten state having the desired complex viscosity $\eta^*$.

According to the present invention a moisture vapour permeable, liquid impervious layer can be formed from the thermoplastic composition of the present invention by coating said thermoplastic composition onto a substrate. The films or layers formed from the thermoplastic compositions of the present invention preferably have a moisture vapour transport rate of at least 100 g/m$^2$·24 h, preferably at least 300 g/m$^2$·24 h, most preferably at least 500 g/m$^2$·24 h.

A process for making a layer or film from a thermoplastic composition according to the present invention typically comprises the steps of providing said composition, heating it to make it flowable, and coating said composition in the molten state onto a substrate in a layer having the desired thickness. While said substrate can be simply a formation substrate, onto which the thermoplastic composition is coated in order to form a film or layer of the desired thickness which is subsequently separated from said substrate and used as such, in an embodiment of the present invention a moisture vapour permeable, water impervious composite can also be formed which comprises the thermoplastic composition and a substrate onto which said thermoplastic composition is coated, wherein the substrate is also preferably moisture vapour permeable.

Such embodiment of the present invention provides a moisture vapour permeable, liquid impervious composite wherein the contribution of the layer formed from the thermoplastic composition of the present invention to the performance of the composite material resides only in the provision of a liquid barrier and hence could be advantageously provided as thinly as possible. The remaining performance physical criterion being preferably provided by the provided substrate, that therefore preferably acts also as a support layer.

The substrate, or support layer may be any useful layer which is preferably also moisture vapour permeable, preferably having a moisture vapour permeability of at least 100 g/m$^2$·24 h, more preferably at least 300 g/m$^2$·24 h, and most preferably at least 500 g/m$^2$·24 h.

Suitable substrates for use herein as support layers include two dimensional, planar micro and macro-porous films; macroscopically expanded films; formed apertured films; nonwoven and woven layers. According to the present invention the apertures in said layer may be of any configuration, but are preferably spherical or oblong and may also be of varying dimensions. The apertures preferably are evenly distributed across the entire surface of the layer, however layers having only certain regions of the surface having apertures are also envisioned.

Suitable two dimensional porous planar layers of the backsheet may be made of any material known in the art, but are preferably manufactured from commonly available polymeric materials. Suitable materials are for example Goretex™ or Sympatex™ type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term two dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured performed films are uni directional such that they have at least substantially, if not complete one directional fluid transport towards the core.

Suitable macroscopically expanded films for use herein include films as described in for example in U.S. Pat. Nos. 4,637,819 and 4,591,523.

Preferred support layers for use herein include woven and nonwoven layers, most preferably hydrophobic fibrous layers such as hydrophobic nonwoven.

The composites of this preferred embodiment of the present invention are particularly advantageous as they allow the possibility of providing a composite wherein the thermoplastic composition may be coated onto the support substrate as a layer with the desired thickness. Typical coating conditions and apparatuses known in the art for the direct coating of low viscosities hot melts can be readily utilised in order to provide the thermoplastic composition at the desired thickness.

A possible method for forming a composite laminate by coating the thermoplastic composition onto a substrate acting as a support layer is described in PCT application WO 96/25902.

At least at the coating temperature, the thermoplastic composition in form of a layer preferably exhibits adhesive properties on the supportive substrate in order to form the preferred composite such that no additional adhesive is required to achieve a permanent attachment between the thermoplastic composition and the substrate. In some applications it may be also desirable that the thermoplastic composition remains tacky at any temperature i.e. it is formulated so to have the typical characteristics of a pressure sensitive adhesive.

The thermoplastic compositions of the present invention and the moisture vapour permeable, liquid impervious layers and composites formed therefrom find utility in a number of applications wherein liquid imperviousness and moisture vapour permeability are desirable. In particular the present invention can be effectively utilised within absorbent articles such as diapers, sanitary napkins, panty liners and incontinence products; perspiration pads such as underarm-, wrist- and head perspiration pads, collar inserts, shoe inserts, hat bands and breast pads; protective bedding covers, protective clothing and the like. Preferably the moisture vapour permeable, liquid impervious layers and composites formed from the thermoplastic compositions of the present invention have a moisture vapour transfer rate of at least 100 g/m$^2$·24 h, more preferably at least 300 g/m$^2$·24 h, and most preferably at least 500 g/m$^2$·24 h.

A moisture vapour permeable, liquid impervious composite structure formed by coating the thermoplastic composition of the present invention onto a suitable substrate finds particular utility as the backsheet for absorbent articles especially sanitary napkins and panty liners. Such articles will typically comprise components known to the skilled person such as a liquid pervious topsheet, an absorbent core and backsheet and may optionally comprise fastening means, wings, and the like.

The preferred hydrophilic plasticisers of the present invention can also be added to thermoplastic polymers which are not intrinsically moisture vapour permeable, such as polyolefins, e.g. polyethylene or polypropylene, or styrenic black copolymers, which are all substantially both moisture vapour and liquid impervious, in order to provide the final thermoplastic composition with moisture vapour permeability.

According to the present invention the complex viscosity η* is measured using a Rheometer RDA-II available from Rheometrics Co. Moisture vapour permeability is measured as Water Vapour Transmission Rate (WVTR) at 23° C. according to the ASTM E-96 "Upright Cup" method.

What is claimed is:

1. A continuous film or layer formed from a thermoplastic composition comprising:
    a thermoplastic polymer or mixture of polymers selected from the group consisting of polyurethanes, poly-ether-amides block copolymers, polyethylene-acrylic acid copolymers, polyethylene oxide and its copolymers, poly lactide and copolymers, polyanides, polyester block copolymers, sulfonated polyesters, poly-ether-ester block copolymers, poly-ether-ester-amide block copolymers, polyacrylates, polyacrylic acids, ionomers, polyethylene-vinyl acetate with a vinyl acetate content of more than 28 weight %, polyvinyl alcohol and its copolymers, polyvinyl ethers and their copolymers, poly-2-ethyl-oxazoline, polyvinyl pyrrolidone and its copolymers, and mixtures thereof,
    a suitable compatible hydrophilic plasticiser blend of hydrophilic plasticisers,
    said thermoplastic composition having a viscosity of from 50 poise to 4000 poise at a frequency of 1 rad/s at a temperature of 210° C. or less and a viscosity of less than 2000 poise at a frequency of 1000 rad/s at a temperature of 210° C. or less,
    wherein said compatible hydrophilic plastcisers are selected from the group consisting of acids, esters, amides, alcohols, polyalcohols, and mixtures thereof,
    and wherein said continuous film or layer is liquid impervious and has a water vapour transmission rate of at least 300 g/m$^2$·24 h, said water vapour transmission rate measured at 23° C. according to the ASTM E-96 "Upright Cup" method.

2. A thermoplastic composition according to claim 1, wherein said composition comprises:
    from 10% to 80% by weight of said thermoplastic composition, of said polymer or mixture of polymers,
    from 20% to 90% by weight of said thermoplastic composition, of said plasticiser or blend of plasticisers,
    from 0 to 50% by weight of a suitable compatible tackifyer resin.

3. A thermoplastic composition according to claim 1, wherein said composition comprises:
    from 25% to 70% by weight of said thermoplastic composition, of said polymer or mixture of polymers,
    from 30% to 75% by weight of said thermoplastic composition, of said plasticiser or blend of plasticisers,
    from 0% to 50% by weight of a suitable compatible tackifyer resin.

4. A thermoplastic composition according to claim 1, wherein said thermoplastic polymer or mixture of polymers comprises thermoplastic poly-ether-amide block copolymers, thermoplastic poly-ether-ester-amide block copolymers, thermoplastic polyester block copolymers, thermoplastic polyurethanes, or mixtures thereof.

5. A thermoplastic composition according to claim 1, wherein said hydrophilic plasticiser is selected from the group consisting of citric acid esters, tartaric acid esters, glycerol and its esters, sorbitol, glycolates, and mixtures thereof.

6. A thermoplastic composition according to claim 1, wherein said tackifier resins are selected from rosins and rosin esters, hydrocarbon resins, aliphatic resins, terpene and terpene-phenolic resins, aromatic resins, synthetic $C_5$ resins, mixtures of synthetic $C_5$–$C_9$ resins, and mixtures thereof.

7. A moisture vapour permeable layer formed from the thermoplastic composition of claim 1, wherein said layer is liquid impervious and has a water vapour transmission rate (WVTR) of at least 300 g/m$^2$·24 h with a thickness of said layer of at least 0.5 μm.

8. A moisture vapour permeable, liquid impervious composite comprising the layer of claim 7 coated onto a substrate, said substrate being moisture vapour permeable.

9. An absorbent article comprising a moisture vapour permeable, liquid impervious layer according to claim 7.

10. An absorbent article comprising a moisture vapour permeable, liquid impervious composite according to claim 8.

11. A process for making a thermoplastic composition according to claim 1, comprising the steps of:
    providing said thermoplastic polymer or mixture of polymers,
    providing said suitable compatible hydrophilic plasticiser or blend of hydrophilic plasticisers,
    heating said thermoplastic polymer or mixture of polymers and said plasticiser or blend of plasticisers and compounding them to form said thermoplastic composition in the molten state.

12. A process for making a layer from the thermoplastic composition of claim 1, comprising the steps of:
    providing said thermoplastic composition,
    heating said thermoplastic composition to make it flowable,
    coating said thermoplastic composition onto a substrate in a layer having a desired thickness.

* * * * *